(12) United States Patent
Richart

(10) Patent No.: US 9,790,015 B2
(45) Date of Patent: Oct. 17, 2017

(54) PACKAGING, PREFERABLY MEDICAL, INCLUDING TWO PACKAGING ELEMENTS

(71) Applicant: SELENIUM MEDICAL, La Rochelle (FR)

(72) Inventor: Oliver Richart, Lagord (FR)

(73) Assignee: SELENIUM MEDICAL, La Rochelle (FR)

( * ) Notice: Subject to any disclaimer, the term of this patent is extended or adjusted under 35 U.S.C. 154(b) by 0 days.

(21) Appl. No.: 14/892,272

(22) PCT Filed: May 26, 2014

(86) PCT No.: PCT/FR2014/051223
§ 371 (c)(1),
(2) Date: Nov. 19, 2015

(87) PCT Pub. No.: WO2014/191668
PCT Pub. Date: Dec. 4, 2014

(65) Prior Publication Data
US 2016/0095663 A1    Apr. 7, 2016

(30) Foreign Application Priority Data
May 27, 2013    (FR) .................................... 13 54751

(51) Int. Cl.
*A61B 17/06* (2006.01)
*B65D 77/04* (2006.01)
(Continued)

(52) U.S. Cl.
CPC ........ *B65D 77/046* (2013.01); *A61B 19/0271* (2013.01); *A61B 50/30* (2016.02);
(Continued)

(58) Field of Classification Search
USPC .................................................. 206/438, 370
See application file for complete search history.

(56) References Cited

U.S. PATENT DOCUMENTS 5,031,768 A * 7/1991 Fischer .................. A61B 50/36
206/364
5,117,981 A * 6/1992 Crawford .................. E06B 9/44
206/370
(Continued)

FOREIGN PATENT DOCUMENTS
FR    2876086    4/2006

OTHER PUBLICATIONS
Search Report dated 2014.

*Primary Examiner* — Jacob K Ackun
(74) *Attorney, Agent, or Firm* — Ipsilon USA, LLP

(57) ABSTRACT

The invention relates to an assembly comprising a transparent "outer" packaging element (1) defining a chamber, and an "inner" packaging element (2) received in said chamber of the outer packaging element (1). Said inner packaging element (2) comprises at least first and second packaging portions (21, 22) that are transparent, each of which has at least one cavity (41, 42) for receiving an article, and a sealing sheet that is at least partially opacifying, and that comprises two portions applied over the two packaging portions (21, 22) in such a manner as to close said cavities (41, 42). The two packaging portions (21, 22) of the inner packaging element (2) are folded over towards each other towards a configuration in which the two portions of said sealing sheet applied over the two packaging portions (21, 22) of the inner packaging element (2) face each other.

11 Claims, 6 Drawing Sheets

(51) Int. Cl.
*A61F 2/00* (2006.01)
*A61B 19/02* (2006.01)
*A61B 50/33* (2016.01)
*A61B 50/00* (2016.01)
*A61B 50/30* (2016.01)

(52) U.S. Cl.
CPC ............ *A61B 50/33* (2016.02); *A61F 2/0095* (2013.01); *A61B 2019/0219* (2013.01); *A61B 2019/0278* (2013.01); *A61B 2019/0286* (2013.01); *A61B 2050/0065* (2016.02); *A61B 2050/3008* (2016.02); *A61B 2050/314* (2016.02)

(56) References Cited

U.S. PATENT DOCUMENTS

| | | | | |
|---|---|---|---|---|
| 5,325,965 | A * | 7/1994 | Kelley | A61M 5/3205 206/366 |
| 8,100,263 | B2 * | 1/2012 | Vanderbush | A61M 5/002 206/366 |
| 2006/0282045 | A1 | 12/2006 | Wilkinson et al. | |
| 2011/0186456 | A1 | 8/2011 | Bertazzoni et al. | |
| 2011/0214398 | A1 | 9/2011 | Liburd et al. | |
| 2012/0158128 | A1 | 6/2012 | Gautam et al. | |
| 2013/0277261 | A1 * | 10/2013 | Kinyon | A61F 2/0095 206/438 |

* cited by examiner

PACKAGING, PREFERABLY MEDICAL, INCLUDING TWO PACKAGING ELEMENTS

RELATED APPLICATIONS

This application is a National Phase Application of PCT/FR2014/051223, filed on May 26, 2014, which in turn claims the benefit of priority from French Patent Application No. 13 54751 filed on May 27, 2013, the entirety of which are incorporated herein by reference.

BACKGROUND

Field of the Invention

The present invention relates generally to packaging elements for packaging articles, and in particular for packaging medical-use parts that are preferably sterilized.

Description of Related Art

A nested packaging assembly of two packaging elements is known from the state of the art that comprises an "outer" first packaging element and an "inner" second packaging element that is received in the outer packaging element and that contains a plurality of medical articles. Said inner packing element is in the form of a blister-pack plate having an "access" face that defines a plurality of distinct blind cavities, each of which receives a respective medical article. Said access face is covered with a sealing sheet that closes each cavity.

The outer packaging element is generally in the form of a tray that defines a chamber in which the inner packaging element is received and which is closed by a sealing sheet. The use of nested packaging having two packaging elements makes it possible to limit the risks of the medical articles packaged in them being contaminated. However, it is observed that the articles packaged in such a manner in a blister-pack plate that is sealed and that is received in a tray that is also sealed are difficult to see, so that users waste precious time identifying the medical articles they need.

OBJECTS AND SUMMARY

An object of the present invention is to propose a novel assembly of packaging elements containing a plurality of articles that are easier to see while also preserving packaging that limits the risk of said articles being contaminated.

To this end, the invention provides an assembly that is preferably medical and that comprises a transparent "outer" packaging element defining a chamber and an "inner" packaging element received in said chamber of the outer packaging element, said inner packaging element comprising at least first and second packaging portions that are transparent, each of which has at least one cavity for receiving an article, and a sealing sheet that is at least partially opacifying, and that comprises two portions applied over the two packaging portions in such a manner as to close said cavities, said assembly being characterized in that the two packaging portions of the inner packaging element are folded over towards each other towards a configuration in which the two portions of said sealing sheet applied over the two packaging portions of the inner packaging element face each other.

By means of the first and second portions of the inner packaging element being folded over one against the other by bringing the corresponding portions of the sealing sheet to face each other, the visibility of the articles contained in each packaging portion is improved because they can be seen through the transparent packaging portions and through the transparent outer packaging. The sealing sheet that is at least partially opacifying does not adversely affect the visibility of the articles contained in the inner packaging element because the sealing sheet, by being folded over, finds itself in the center of the folded inner packaging element, and because said articles can be seen through the transparent portions of the inner and outer packaging elements that are situated facing one another. In addition, packaging in the form of nested packaging with each cavity being sealed makes it possible to limit the risk of said articles being contaminated.

In accordance with an advantageous characteristic of the invention, the inner packaging element is provided with grip means that are accessible on opening the outer packaging element.

In accordance with an advantageous characteristic of the invention, said inner packaging element further comprises a third packaging portion that is transparent and that extends between the first and second portions of said inner packaging, said third packaging portion element being provided with as least one article-receiving cavity that is closed by a third portion of the sealing sheet.

In accordance with an advantageous characteristic of the invention, the first and second packaging portions of the inner packaging element are separated from each other by at least one fold line.

In accordance with an advantageous characteristic of the invention, each of the first and second packaging portions is separated from the third packaging portion by two fold lines that are mutually parallel and that are spaced apart.

In accordance with an advantageous characteristic of the invention, said packaging portions of the inner packaging element are made in one piece. Preferably, the inner packaging element is in the form of a foldable plate in which said cavities are formed.

In accordance with an advantageous characteristic of the invention, said packaging portions of the inner packaging element are disjoint from one another, and said sealing sheet that closes the cavities of said packaging portions interconnects said packaging portions of the inner packaging element.

Preferably, the sealing sheet of the inner packaging element is applied over said packaging portions of the inner packaging element under pressure and while hot.

In accordance with an advantageous characteristic of the invention, said outer packaging element comprises an open body that is preferably rectangular box shaped, and that has its opening closed by a sealing sheet applied over the peripheral margin of the opening.

Advantageously, said or each sealing sheet is impermeable to liquids and to bacteria.

BRIEF DESCRIPTION OF THE DRAWINGS

The invention can be well understood on reading the following description of embodiments given with reference to the accompanying drawings, in which.

DETAILED DESCRIPTION

Figure 1:
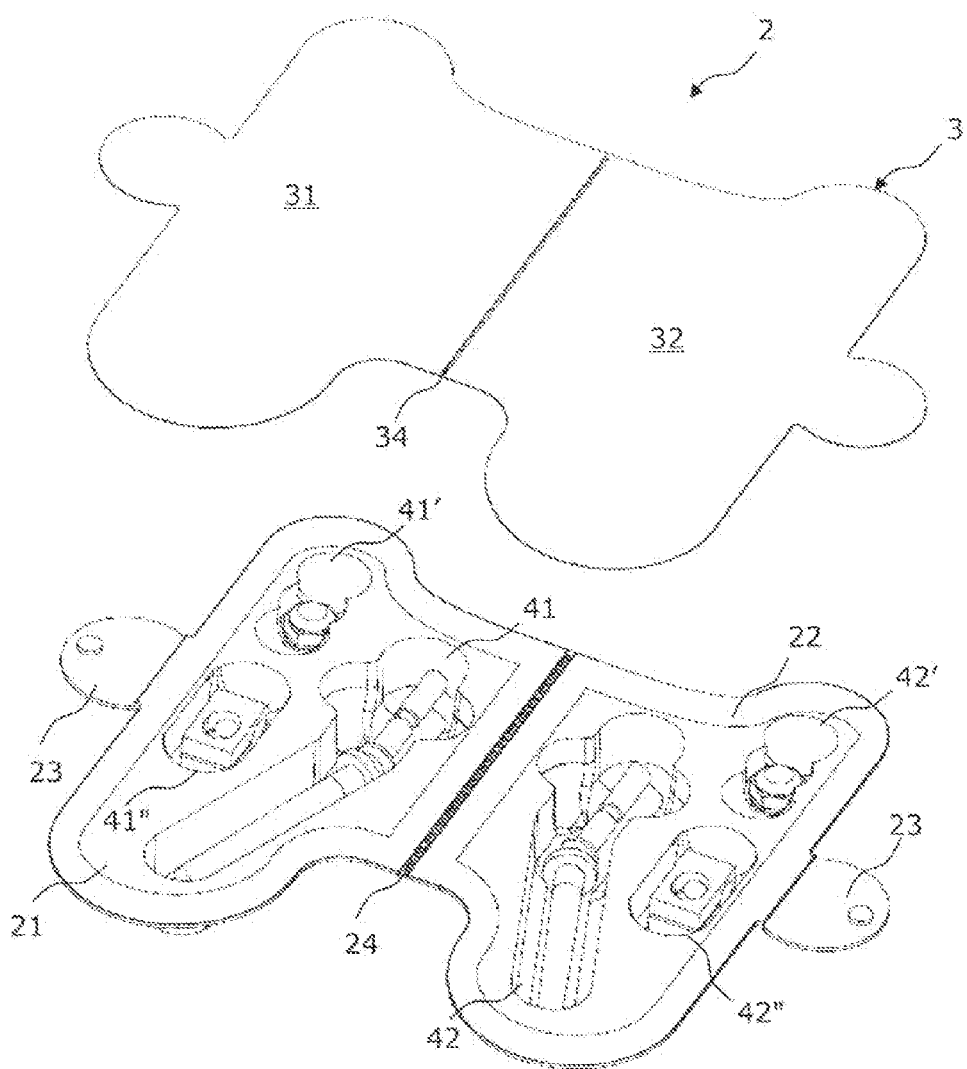
FIG. 1 is an exploded flat view of a first embodiment of an inner packaging element of the invention that comprises two packaging portions, each of which has a plurality of cavities designed to be closed by a suitable sealing sheet.

With reference to the figures and as stated above, the invention relates to a preferably medical assembly comprising a transparent "outer" packaging element 1 and an "inner" packaging element 2 that is received in said outer packaging element 1.

Said outer packaging element 1 comprises an open body having its opening 130 closed by a sealing sheet 13 applied as described in detail below over the peripheral margin 131 of the opening.

In more general manner, the outer packaging element 1 is sealed in a manner impermeable to liquids and to bacteria. The sealing zone can be destroyed by the user in order to access the contents of said outer packaging element.

Figure 2:
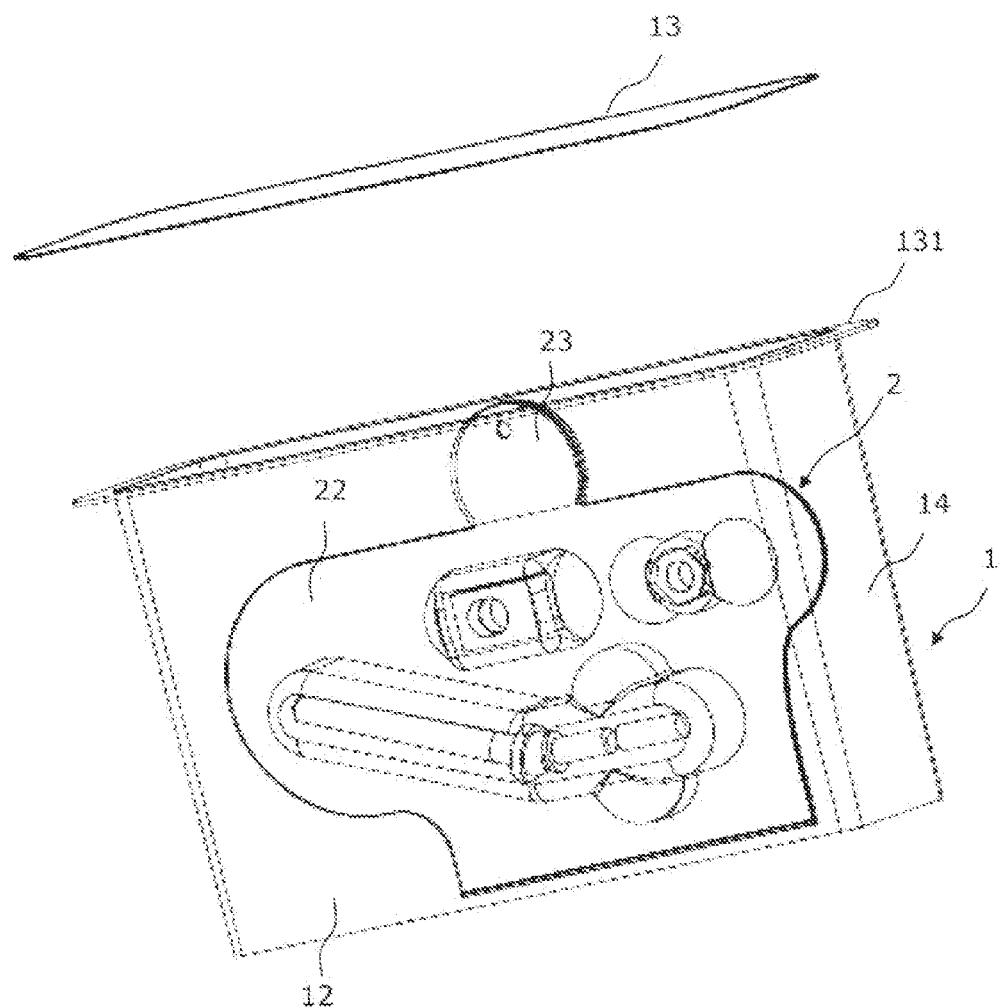
FIG. 2 is a view of the FIG. 1 inner packaging element in the state in which the two packaging portions of the inner packaging element are folded over one on the other, and in the state received in the chamber defined by an outer packaging element having its opening designed to be closed by a suitable sealing sheet.
Figure 2A:
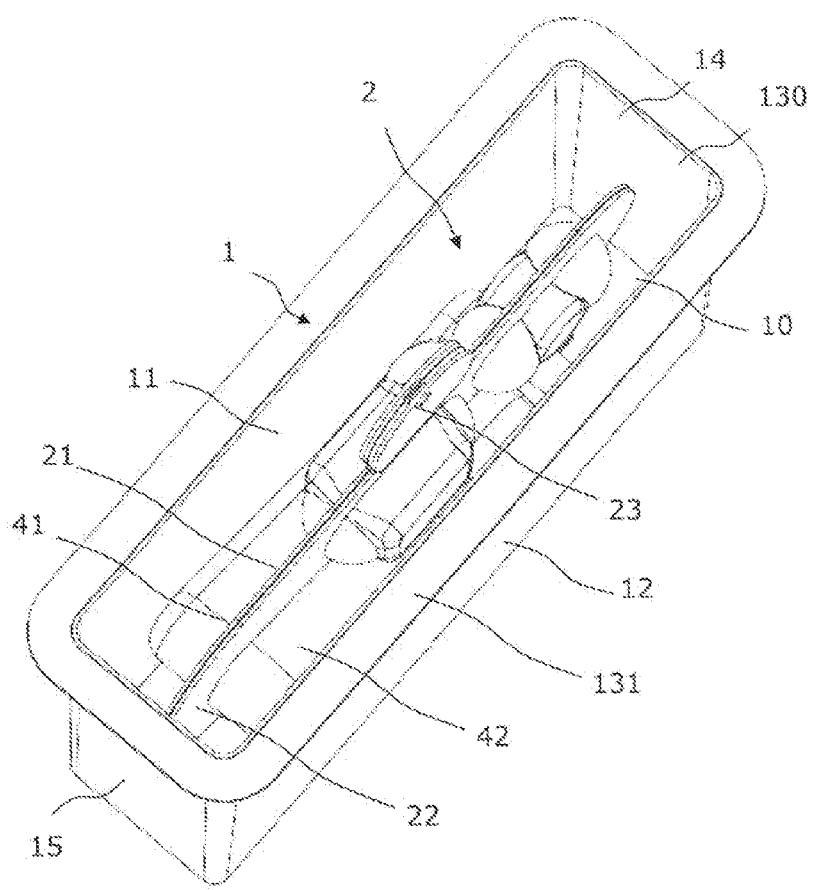
FIG. 2A is a view from above of the outer packaging element and of the FIG. 1 inner packaging element.
Figure 4:
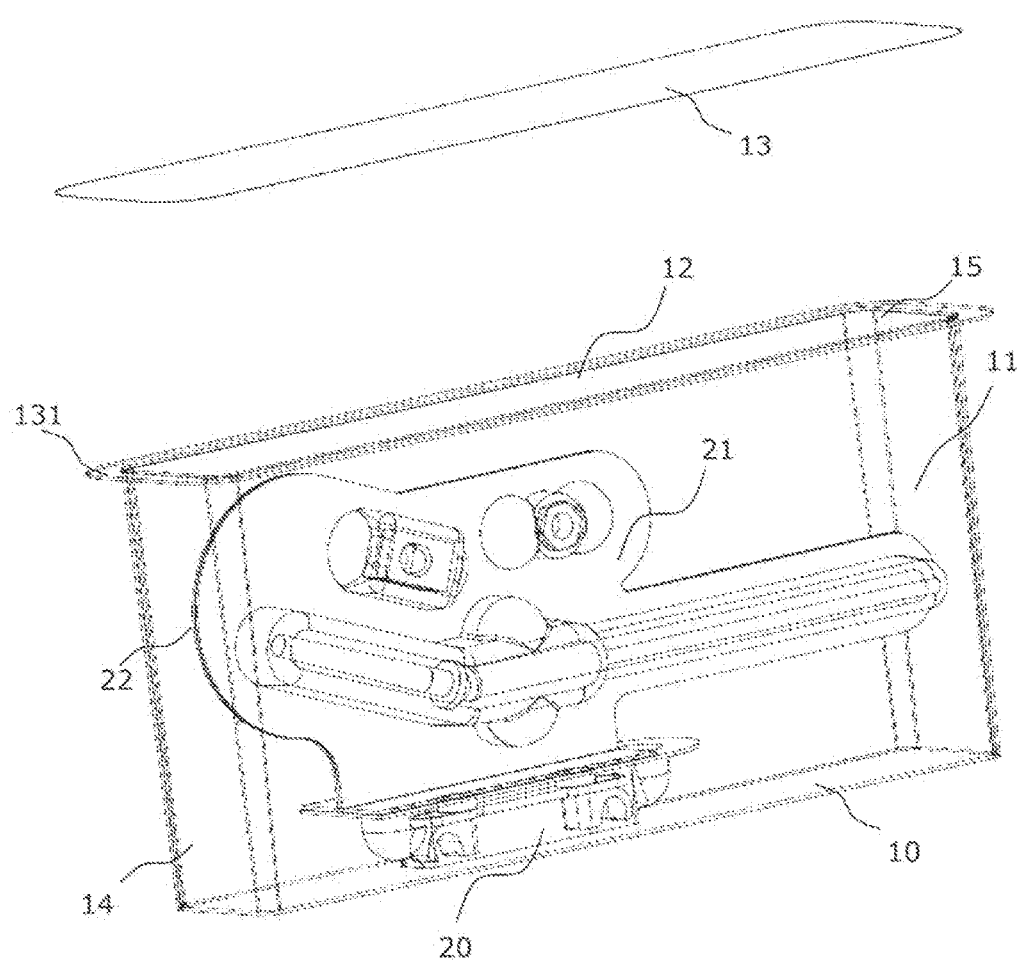
FIG. 4 is a view of the FIG. 3 inner packaging element in the state in which two opposite portions of the packaging element are folded over one on the other, and in the state received in the chamber defined by an outer packaging element having its opening designed to be closed by a suitable sealing sheet.

In the example shown in FIGS. 2, 2A, and 4, said outer packaging element 1 is thus in the form of a rectangular box having one face open 130 and closed off by the sealing sheet 13. In an embodiment, said sealing sheet 13 is at least partially opacifying in contrast to the transparency of the packaging element.

Said sealing sheet 13 is a heat-sealable, peel-off sheet that is, for example, made of a non-woven synthetic material manufactured from polyethylene fibers and usually sold under the registered trademark Tyvek.

Said outer packaging element 1 thus has an end-wall or "bottom" wall 10 opposite from the opening 130 of the outer packaging element 1 and two large opposite side walls 11, 12 connected together by two other smaller opposite side wails or "end walls" 14, 15.

Said inner packaging element 2 comprises at least first and second packaging portions 21, 22 that are transparent, and each of which is provided with at least one cavity 41, 42. Said cavities 41, 42 are distinct and separate, i.e. they do not communicate with one another. Each cavity contains a preferably medical article.

For example, said article may be a solid part, such as a screw for surgery, or any other type of article, and in particular any other type of implant. In addition, said article may be a liquid or a powder. Said article, and preferably the various portions of the packaging element, are sterilized, e.g. by radiation.

The assembly is designed for the purposes of preserving the sterility of each article contained in the inner packaging element 2, and with a view to unpacking the article under aseptic or nearly aseptic conditions.

In the example shown in the figures, each packaging portion 21, 22 has three cavities, respectively 41, 41', & 41", and 42, 42', & 42", each of which receives a respective article as explained below.

The inner packaging element 2 is in the form of a foldable plate in which cavities are formed. Said inner packaging element 2 and the outer packaging element 1 are preferably thermoformed. In a variant, each packaging element may be made by molding, e.g. by injection molding.

When the inner packaging element 2 is in the unfolded and flat state, the openings of the cavities open out on the same side of said plate that forms the inner packaging element 2.

A sealing sheet 3 is applied over both packaging portions 21, 22 in such a manner as to close said cavities and as to keep the articles contained in them protected from external contamination. Like the sealing sheet 13, said sealing sheet 3 is at least partially opacifying in contrast to the transparency of the packaging element. Advantageously, said sealing sheet 3 is a heat-sealable, peel-off sheet that is, for example, made of a non-woven synthetic material manufactured from polyethylene fibers and usually sold under the registered trademark Tyvek.

The sealing sheet 3 of the inner packaging element 2 is applied over said packaging portions of the inner packaging element 2 under pressure and while hot, i.e. by heat-sealing. Similarly, the sealing sheet 13 of the outer packaging element 1 is also applied by heat-sealing over the opening in the outer packaging element 1.

The two packaging portions 21 & 22 are folded over towards each other, and towards a configuration in which the two portions 31 & 32 of the sheet 3 that are applied over the corresponding ones of the two packaging portions 21 & 22 of the inner packaging element 2 face each other. In the example shown in the figures, the portions of the sealing sheet 3 that are applied over the packaging portions of the inner packaging element 2 are made in one piece with one another. Breakable or score lines are merely provided between said portions of the sealing sheet 3. In a variant not shown, provision may be made for said portions of the sealing sheets 3 to be disjoint from one another and for the sheet 3 thus to be formed of a plurality of pieces.

In the example, shown in FIG. 1, the first and second packaging portions 21, 22 of the inner packaging element 2 are separated from each other by a fold line 24. In similar manner, the two portions 31, 32 of the sheet 3 that are applied are also separated from each other by a fold line 34.

Thus, in the example shown in the figures, one (21) of the two packaging portions 21, 22 of the inner packaging element 2 extends facing the side wall 11 of the outer packaging element 1 and the other (22) of said two packaging portions extends facing the other side wall 12 of the outer packaging element 1. In other words, one (21) of the packaging portions 21, 22 can be seen from one side of the outer packaging element 1 and the other packaging portion 22 can be seen from the other side.

In a variant not shown, provision may be made for the outer packaging element to be formed of two shells suitable for defining between them said chamber that receives the inner packaging element.

In general manner, the chamber defined by said outer packaging element 1 can be opened by breaking open a sealing zone and/or by separating two assembled-together portions, such as two shells suitable for being assembled together.

The sealing sheet 3 is not transparent so that folding the portions 31, 32 of the sheet 3 over onto each other makes it possible to position the sheet substantially in the centre of the outer packaging element 1 and to place the corresponding packaging portions 21, 22 of the inner packaging element 2, which portions are transparent, on the same side as the wall(s) of the outer packaging element 1, which is also transparent.

As shown in the figures, the inner packaging element 2 is provided with grip means 23 for taking hold of the inner packaging element 2, which grip means are accessible on opening the outer packaging element 1. As stated above, said opening 130 of the outer packaging element 1 is closed by the sealing sheet 13. Said packaging element is also provided with retaining means of the male-female type, for keeping the packaging portions 21, 22 folded over against each other, which retaining means are deactivatable. In the example shown in FIGS. 1 and 5, these retaining means are provided on the grip means 23 in the form of a male element provided on a tongue 23 associated with the packaging portion 21 and of a female element provided on a tongue 23 associated with the packaging portion 22.

Figure 3:
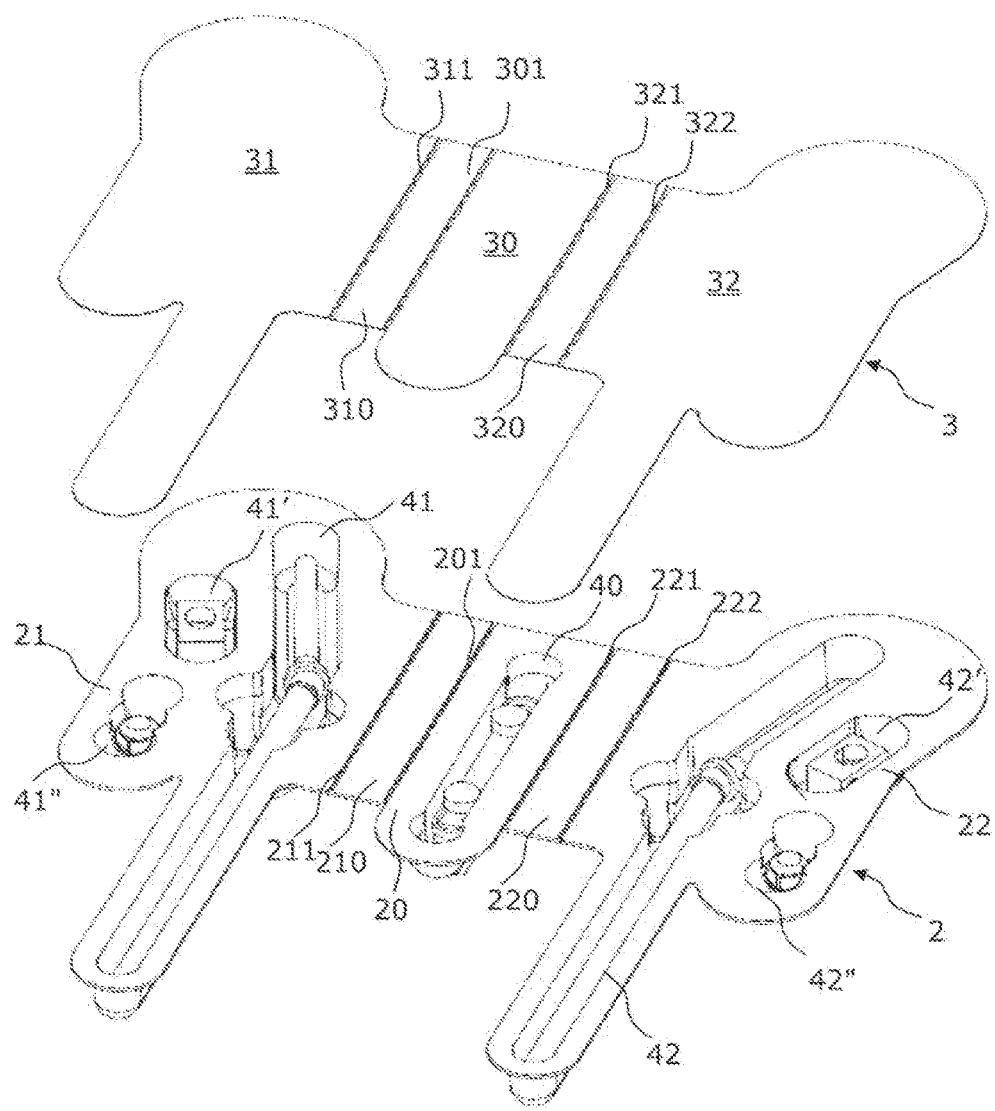
FIG. 3 is an exploded flat view of a second embodiment of an inner packaging element of the invention that comprises three packaging portions, each of which has a plurality of cavities designed to be closed by a suitable sealing sheet.
Figure 5:
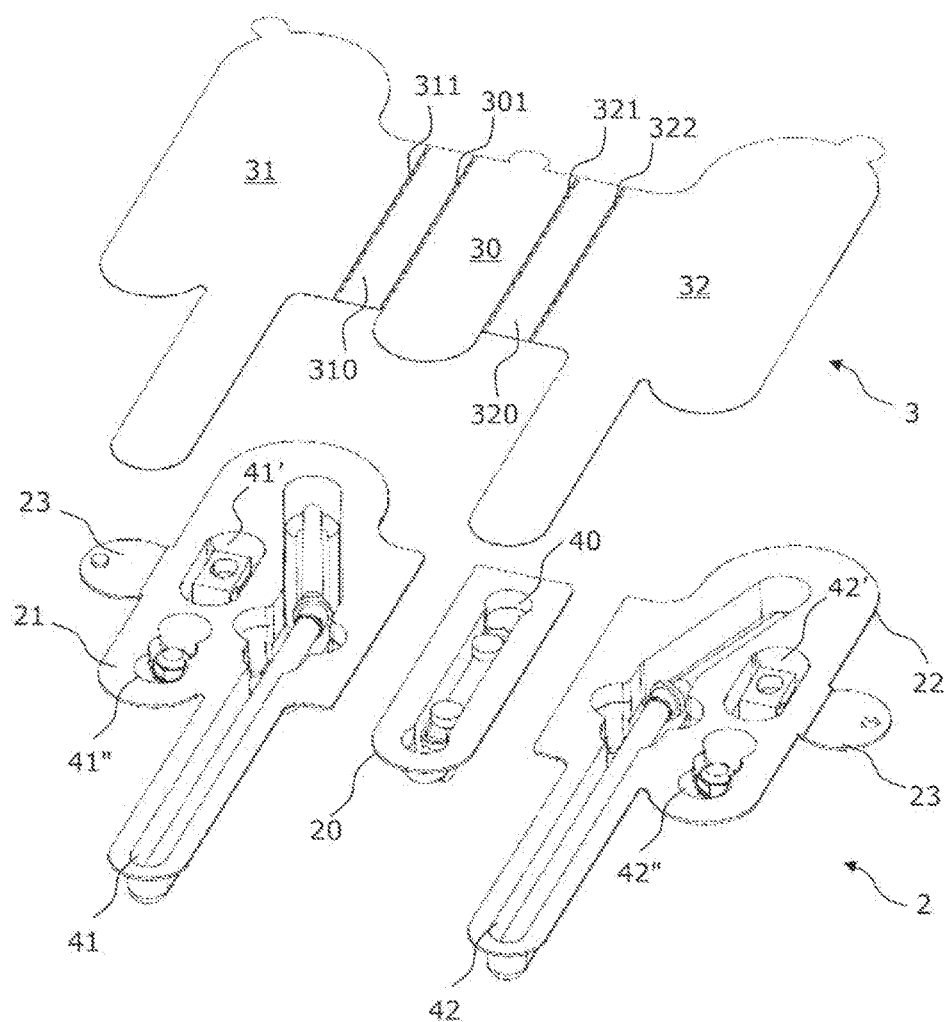
FIG. 5 is a variant embodiment of the FIG. 3 inner packaging element in which the various portions of the packaging element are mutually disjoint and are connected together by the sealing sheet.

In an embodiment shown in FIGS. 3 to 5, said inner packaging element 2 further comprises a transparent third packaging portion 20 that is interposed between the first and second packaging portions 21, 22. Said third packaging portion 20 includes an article-receiving cavity 40 that is closed by a third portion 30 of the sealing sheet 3.

In the example shown in FIGS. 3 and 4, each of the first and second packaging portions 21, 22 is separated from the third packaging portion 20 by two fold lines 211, 201, 221, 222 that are mutually parallel and that are spaced apart from each other.

Regardless of whether it is for the embodiment shown in FIGS. 1 to 2A or for the embodiment shown in FIGS. 3 and 4, the or each fold line may be formed by a line of discontinuous perforations making it possible not only to fold the packaging element about said line but also to tear it or to break it along said line.

The sealing sheet also has corresponding fold lines 311 & 301 and 321 & 322 that define between them respective link portions 310, 320 between the portions 31, 32, and 30 of the sealing sheet 3.

In the example shown in FIGS. 3 and 4, said third packaging portion 20 of the inner packaging element 2 faces the end-wall 10 of the outer packaging element, while the third portion 30 of the sealing sheet 3 faces towards the opening 130 of said outer packaging element. In the same way as for the embodiment shown in FIGS. 1 to 2A, the first and second portions 21 & 22 of the inner packaging element 2 having their cavities closed by the portions 31 & 32 of the sealing sheet 3 may be folded towards each other towards a configuration in which said portions 31 & 32 of the sheet 3 face each other. The link portions 210 & 220 of the inner packaging element 2 that are defined respectively between the fold lines 211 & 201, and between the fold lines 221 & 222 are then folded over towards the third portion 20 of the inner packaging element 2 towards a configuration in which the corresponding link portions 310, 230 of the sealing sheet face the third portion 30 of said sheet that covers the portion 20 of the inner packaging element 2.

In a variant embodiment shown in FIG. 5, said packaging portions 20, 21, 22 of the inner packaging element 2 are disjoint from one another. The sealing sheet 3 that closes the cavities 40, 41, 41', 41", 42, 42', 42" of said packaging portions 20, 21, 22 interconnects said portions 20, 21, 22 of the inner packaging element 2. In other words, the disjoint portions of the inner packaging element 2 are interconnected by a sealing sheet 3 made in one piece.

In order to unpack one or more articles contained in the assembly and in particular in the inner packaging element 2, it is possible to proceed as follows.

People working under non-aseptic conditions who might contaminate with their hands the articles they touch can be considered to be "dirty" or "contaminated". Conversely, people working under sufficiently aseptic conditions can be considered to be "clean".

After having visually identified the desired article (s) through the outer packaging element 1, and the portions of the inner packaging element 2 that are situated facing the wall(s) of the outer packaging element 1, a first person, assumed to be in a contaminated zone, removes the sealing strip 13 from the outer packaging element 1 so as to provide access to the inner packaging element 2.

Said "contaminated" first person can thus hold out the inner packaging element 2 without touching it, by holding the outer packaging element 1. The inner packaging element 2 can then be taken hold of by a second person, who is assumed to be in a clean zone. After having taken hold of the inner packaging element 2, preferably by the grip zone 23, said clean person can then remove the or each portion of the sealing sheet 3 of the inner packaging element 2 that closes the or each cavity corresponding to the desired article or to each desired article so as to take hold of the article contained in said or each cavity. Said "clean" person is, for example, a surgeon in an operating theater.

It is also possible to make provision for the clean person to separate, e.g. by cutting along the fold lines, the packaging portion that contains the desired article from the remaining portion of the inner packaging element, in such a manner as only to open the cavity that contains the desired article.

Thus, the or each article contained in a cavity of the inner packaging element 2 has never been touched or released while it is being unpacked. In addition, the or each cavity of the inner packaging element 2 containing the or each article is opened only once in a clean zone.

The present invention is in no way limited to the embodiments described and shown, and the person skilled in the art can make any variant to them that lies within the spirit of the invention.

The invention claimed is:

1. An assembly, that is preferably medical, comprises:
   a transparent "outer" packaging element defining a chamber; and
   an "inner" packaging element received in said chamber of the outer packaging element;
   said inner packaging element comprising at least first and second packaging portions that are transparent, each of which has at least one cavity for receiving an article, and a sealing sheet that is at least partially opacifying, and that comprises two portions applied over the two packaging portions in such a manner as to close said cavities;
   wherein the two packaging portions of the inner packaging element are folded over towards each other towards a configuration in which the two portions of said sealing sheet applied over the two packaging portions of the inner packaging element face each other.

2. An assembly according to claim 1, wherein the inner packaging element is provided with grip means that are accessible on opening the outer packaging element.

3. An assembly according to claim 1, wherein said inner packaging element further comprises a third packaging portion that is transparent and that extends between the first and second portions, said third packaging portion of said inner packaging element being provided with at least one article-receiving cavity that is closed by a third portion of the sealing sheet.

4. An assembly according to claim 1, wherein the first and second packaging portions of the inner packaging element are separated from each other by at least one fold line.

5. An assembly according to claim 4, wherein each of the first and second packaging portions is separated from the third packaging portion by two fold lines that are mutually parallel and that are spaced apart.

6. An assembly according to claim 1, wherein said packaging portions of the inner packaging element are made in one piece.

7. An assembly according to claim 6, wherein the inner packaging element is in the form of a foldable plate in which said cavities are formed.

8. An assembly according to claim 1, wherein said packaging portions of the inner packaging element are disjoint from one another, and in that said sealing sheet that closes the cavities, of said packaging portions interconnects said packaging portions of the inner packaging element.

9. An assembly according to claim 1, wherein the sealing sheet of the inner packaging element is applied over said packaging portions of the inner packaging element under pressure and while hot.

10. An assembly according to claim 1, wherein said outer packaging element comprises an open body that is preferably rectangular box shaped, and that has its opening closed by a sealing sheet applied over the peripheral margin of the opening.

11. An assembly according to claim 1, wherein said or each sealing sheet is impermeable to liquids and to bacteria.

\* \* \* \* \*